United States Patent
Gamache et al.

(10) Patent No.: US 10,973,556 B2
(45) Date of Patent: Apr. 13, 2021

(54) ADJUSTABLE IMPLANT ASSEMBLY

(75) Inventors: Thomas Gamache, Westport, MA (US); Michael Varieur, Portsmouth, RI (US); Kenneth Connell, Rumford, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 1526 days.

(21) Appl. No.: 12/140,412

(22) Filed: Jun. 17, 2008

(65) Prior Publication Data

US 2009/0312804 A1 Dec. 17, 2009

(51) Int. Cl.
| | | |
|---|---|---|
| *A61B 17/04* | (2006.01) | |
| *A61B 17/86* | (2006.01) | |
| *A61F 2/08* | (2006.01) | |
| *A61B 17/84* | (2006.01) | |
| *A61B 17/70* | (2006.01) | |

(52) U.S. Cl.
CPC ........ *A61B 17/704* (2013.01); *A61B 17/7032* (2013.01)

(58) Field of Classification Search
USPC ................................................. 606/308, 266
See application file for complete search history.

(56) References Cited

U.S. PATENT DOCUMENTS

| | | |
|---|---|---|
| 410,780 A | 9/1889 | Cahn |
| 445,513 A | 1/1891 | Powell |
| 1,116,532 A | 11/1914 | Armstrong |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Frederick |
| 2,248,054 A | 7/1941 | Becker |
| 2,248,057 A | 7/1941 | Bond |
| 2,291,413 A | 7/1942 | Siebrandt |
| 2,370,407 A | 2/1945 | Howard |

(Continued)

FOREIGN PATENT DOCUMENTS

| | | |
|---|---|---|
| DE | 3923996 A1 | 1/1991 |
| DE | 9110203 U1 | 11/1991 |

(Continued)

OTHER PUBLICATIONS

Wiltse, Leon L. et al., "History of Pedicle Screw Fixation of the Spine," Spine, State of the Art Reviews, vol. 6(1):1-10 (1992).

(Continued)

*Primary Examiner* — Jacqueline Woznicki
(74) *Attorney, Agent, or Firm* — Nelson Mullins Riley & Scarborough LLP; Anthony A. Laurentano

(57) ABSTRACT

An implant assembly includes a screw body, including anchor portion and proximal head portion, and a cradle movably mounted in the screw body to allow for controlled angulation between a spinal connection element disposed in the cradle and the screw body. The cradle is pivotable in one or more selected directions about one or more axes relative to the screw body. The cradle may be generally, substantially spherical in shape and allow for unrestricted movement in one or more directions around one or more axis.

3 Claims, 7 Drawing Sheets

(56) References Cited

U.S. PATENT DOCUMENTS

| | | |
|---|---|---|
| 2,669,896 A | 2/1954 | Clough |
| 2,800,820 A | 7/1957 | Retterath |
| 2,952,285 A | 9/1960 | Roosli |
| 3,604,487 A | 9/1971 | Gilbert |
| 3,960,147 A | 6/1976 | Murray |
| 4,237,875 A | 12/1980 | Termanini |
| 4,271,836 A | 6/1981 | Bacal et al. |
| 4,363,250 A | 12/1982 | Suga |
| 4,411,259 A | 10/1983 | Drummond |
| 4,445,513 A | 5/1984 | Ulrich et al. |
| 4,655,223 A | 4/1987 | Kim |
| 4,733,657 A | 3/1988 | Kluger |
| 4,743,260 A | 5/1988 | Burton |
| 4,809,695 A | 3/1989 | Gwathmey et al. |
| 4,887,596 A | 12/1989 | Sherman |
| 4,896,661 A | 1/1990 | Bogert et al. |
| 4,950,269 A | 8/1990 | Gaines, Jr. |
| 4,957,495 A | 9/1990 | Kluger et al. |
| 4,987,892 A | 1/1991 | Krag et al. |
| 5,005,562 A | 4/1991 | Cotrel et al. |
| 5,014,407 A | 5/1991 | Boughten et al. |
| 5,020,519 A | 6/1991 | Hayes et al. |
| 5,067,955 A | 11/1991 | Cotrel |
| 5,092,866 A | 3/1992 | Breard et al. |
| 5,120,171 A | 6/1992 | Lasner |
| 5,176,678 A | 1/1993 | Tsou |
| 5,176,680 A | 1/1993 | Vignaud et al. |
| 5,181,917 A | 1/1993 | Rogozinski |
| 5,181,971 A | 1/1993 | Ohtsuka |
| 5,190,543 A | 3/1993 | Schlapfer |
| 5,219,349 A | 6/1993 | Krag et al. |
| 5,226,766 A | 7/1993 | Lasner |
| 5,261,913 A | 11/1993 | Marnay |
| 5,263,939 A | 11/1993 | Wortrich |
| 5,282,801 A | 2/1994 | Sherman |
| 5,282,863 A | 2/1994 | Burton |
| D346,217 S | 4/1994 | Sparker et al. |
| 5,306,248 A | 4/1994 | Barrington |
| 5,330,474 A | 7/1994 | Lin |
| 5,334,203 A | 8/1994 | Wagner |
| 5,360,431 A | 11/1994 | Puno et al. |
| 5,364,397 A | 11/1994 | Hayes et al. |
| 5,385,565 A | 1/1995 | Ray |
| 5,387,213 A | 2/1995 | Breard et al. |
| 5,391,170 A | 2/1995 | McGuire et al. |
| 5,415,661 A | 5/1995 | Holmes |
| 5,429,641 A | 7/1995 | Goffried |
| 5,431,658 A | 7/1995 | Moskovich |
| 5,468,241 A | 11/1995 | Metz-Stavenhagen et al. |
| 5,478,340 A | 12/1995 | Kluger |
| 5,484,440 A | 1/1996 | Allard |
| 5,487,744 A | 1/1996 | Howland |
| 5,499,983 A | 3/1996 | Hughes |
| 5,501,684 A | 3/1996 | Schlapfer et al. |
| 5,520,689 A | 5/1996 | Schlapfer et al. |
| 5,522,816 A | 6/1996 | Dinello et al. |
| 5,536,127 A | 7/1996 | Pennig |
| 5,536,268 A | 7/1996 | Griss |
| 5,540,688 A | 7/1996 | Navas |
| 5,545,165 A | 8/1996 | Biedermann et al. |
| 5,549,608 A | 8/1996 | Errico et al. |
| 5,551,320 A | 9/1996 | Horobec et al. |
| 5,591,166 A | 1/1997 | Bernhardt et al. |
| 5,591,235 A | 1/1997 | Kuslich |
| 5,616,143 A | 4/1997 | Schlapfer et al. |
| 5,649,931 A | 7/1997 | Bryant et al. |
| 5,667,513 A | 9/1997 | Torrie et al. |
| 5,672,175 A | 9/1997 | Martin |
| 5,672,176 A | 9/1997 | Biedermann et al. |
| 5,683,399 A | 11/1997 | Jones |
| 5,697,933 A | 12/1997 | Gundlapalli et al. |
| 5,702,393 A | 12/1997 | Pfaifer |
| 5,707,371 A | 1/1998 | Metz-Stavenhagen |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,797,910 A | 8/1998 | Martin |
| 5,797,911 A | 8/1998 | Sherman et al. |
| 5,810,878 A | 9/1998 | Burel et al. |
| 5,814,046 A | 9/1998 | Hopf |
| 5,879,350 A | 3/1999 | Sherman et al. |
| 5,882,350 A | 3/1999 | Ralph et al. |
| 5,885,285 A | 3/1999 | Simonson |
| RE36,211 E | 5/1999 | Nonomura |
| RE36,221 E | 6/1999 | Breard et al. |
| 5,910,141 A | 6/1999 | Morrison et al. |
| 5,938,663 A | 8/1999 | Petreto |
| 5,941,885 A | 8/1999 | Jackson |
| 5,951,555 A | 9/1999 | Rehak et al. |
| 5,951,564 A | 9/1999 | Schroder et al. |
| 5,951,579 A | 9/1999 | Dykes |
| 5,964,760 A | 10/1999 | Richelsoph |
| 5,976,133 A | 11/1999 | Kraus et al. |
| 5,989,250 A | 11/1999 | Wagner et al. |
| 5,989,254 A | 11/1999 | Katz |
| 6,010,509 A | 1/2000 | Delgado et al. |
| 6,036,692 A | 3/2000 | Burel et al. |
| 6,050,997 A | 4/2000 | Mullane |
| 6,063,090 A | 5/2000 | Schlapfer |
| 6,073,491 A | 6/2000 | Fischer et al. |
| 6,074,391 A | 6/2000 | Metz-Stavenhagen et al. |
| 6,090,110 A | 7/2000 | Metz-Stavenhagen |
| 6,090,113 A | 7/2000 | Le Couedic et al. |
| 6,099,528 A | 8/2000 | Saurat |
| 6,123,707 A | 9/2000 | Wagner |
| 6,139,549 A | 10/2000 | Keller |
| 6,146,383 A | 11/2000 | Studer et al. |
| 6,183,472 B1 | 2/2001 | Lutz |
| 6,189,422 B1 | 2/2001 | Stihl |
| 6,204,060 B1 | 3/2001 | Mehtali et al. |
| 6,210,330 B1 | 4/2001 | Tepper |
| 6,235,028 B1 | 5/2001 | Brumfield et al. |
| 6,251,112 B1 | 6/2001 | Jackson |
| 6,254,602 B1 | 7/2001 | Justis |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,280,443 B1 | 8/2001 | Gu et al. |
| 6,287,309 B1 | 9/2001 | Baccelli et al. |
| 6,299,616 B1 | 10/2001 | Beger |
| 6,302,888 B1 | 10/2001 | Mellinger et al. |
| 6,309,389 B1 | 10/2001 | Baccelli |
| 6,368,321 B1 | 4/2002 | Jackson |
| 6,371,973 B1 | 4/2002 | Tepper |
| 6,379,357 B1 | 4/2002 | Bernstein et al. |
| 6,402,752 B2 | 6/2002 | Schaffler-Wachter et al. |
| 6,423,065 B2 | 7/2002 | Ferree |
| 6,440,133 B1 | 8/2002 | Beale et al. |
| 6,440,137 B1 | 8/2002 | Horvath et al. |
| 6,440,142 B1 | 8/2002 | Ralph et al. |
| 6,440,144 B1 | 8/2002 | Bacher |
| 6,443,953 B1 | 9/2002 | Perra et al. |
| 6,478,798 B1 | 11/2002 | Howland |
| 6,511,484 B2 | 1/2003 | Torode et al. |
| 6,530,929 B1 | 3/2003 | Justis et al. |
| 6,537,276 B2 | 3/2003 | Metz-Stavenhagen |
| 6,540,748 B2 | 4/2003 | Lombardo |
| 6,554,831 B1 | 4/2003 | Rivard et al. |
| 6,565,567 B1 | 5/2003 | Haider |
| 6,589,249 B2 | 7/2003 | Sater et al. |
| 6,597,279 B2 | 7/2003 | Haraguchi |
| 6,623,485 B2 | 9/2003 | Doubler et al. |
| 6,648,888 B1 | 11/2003 | Shluzas |
| 6,652,523 B1 | 11/2003 | Evrard et al. |
| 6,660,006 B2 | 12/2003 | Markworth et al. |
| 6,689,137 B2 | 2/2004 | Reed |
| 6,692,500 B2 | 2/2004 | Reed |
| 6,695,843 B2 | 2/2004 | Biedermann et al. |
| 6,716,214 B1 | 4/2004 | Jackson |
| 6,726,692 B2 | 4/2004 | Bette et al. |
| 6,733,502 B2 | 5/2004 | Altarac et al. |
| 6,743,231 B1 | 6/2004 | Gray et al. |
| 6,746,449 B2 | 6/2004 | Jones et al. |

(56) References Cited

U.S. PATENT DOCUMENTS

| | | |
|---|---|---|
| 6,749,613 B1 | 6/2004 | Conchy et al. |
| 6,752,832 B2 | 6/2004 | Neumann |
| 6,755,829 B1 | 6/2004 | Bono et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,800,078 B2 | 10/2004 | Reed |
| 6,800,079 B2 | 10/2004 | Reed |
| 6,827,722 B1 | 12/2004 | Schoenefeld |
| 6,837,889 B2 | 1/2005 | Shluzas |
| 6,964,666 B2 | 11/2005 | Jackson |
| 7,081,117 B2 | 7/2006 | Bono et al. |
| 7,083,621 B2 | 8/2006 | Shaolian et al. |
| 7,090,677 B2 | 8/2006 | Fallin et al. |
| 7,156,849 B2 | 1/2007 | Dunbar et al. |
| 7,160,300 B2 | 1/2007 | Jackson |
| 7,179,254 B2 | 2/2007 | Pendekanti et al. |
| 7,179,261 B2 | 2/2007 | Sicvol et al. |
| 7,189,234 B2 | 3/2007 | Zucherman et al. |
| 7,250,052 B2 | 7/2007 | Landry et al. |
| 7,278,995 B2 | 10/2007 | Nichols et al. |
| 7,320,689 B2 | 1/2008 | Keller |
| 7,322,979 B2 | 1/2008 | Crandall et al. |
| 7,371,239 B2 | 5/2008 | Dec et al. |
| 7,455,685 B2 | 11/2008 | Justis |
| 7,462,182 B2 | 12/2008 | Lim |
| 7,465,306 B2 | 12/2008 | Pond, Jr. et al. |
| 7,470,279 B2 | 12/2008 | Jackson |
| 7,485,120 B2 | 2/2009 | Ray |
| 7,491,207 B2 | 2/2009 | Keyer et al. |
| 7,491,208 B2 | 2/2009 | Pond, Jr. et al. |
| 7,491,218 B2 | 2/2009 | Landry et al. |
| 7,527,638 B2 | 5/2009 | Anderson et al. |
| 7,572,281 B2 | 8/2009 | Runco et al. |
| 7,588,585 B2 | 9/2009 | Gold et al. |
| 7,591,836 B2 | 9/2009 | Dick et al. |
| 7,621,918 B2 | 11/2009 | Jackson |
| 7,651,502 B2 | 1/2010 | Jackson |
| 7,666,188 B2 | 2/2010 | Anderson et al. |
| 7,666,189 B2 | 2/2010 | Gerber et al. |
| 7,708,736 B2 | 5/2010 | Mullaney |
| 7,708,763 B2 | 5/2010 | Selover et al. |
| 7,766,944 B2 | 8/2010 | Metz-Stavenhagen |
| 7,794,464 B2 | 9/2010 | Bridwell et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,867,237 B2 | 1/2011 | Stad et al. |
| 7,887,539 B2 | 2/2011 | Dunbar, Jr. et al. |
| 7,887,541 B2 | 2/2011 | Runco et al. |
| 7,951,168 B2 | 5/2011 | Chao et al. |
| 7,951,172 B2 | 5/2011 | Chao et al. |
| 7,951,175 B2 | 5/2011 | Chao et al. |
| 7,988,698 B2 | 8/2011 | Rosenberg et al. |
| 8,007,516 B2 | 8/2011 | Chao et al. |
| 8,172,847 B2 | 5/2012 | Dziedzic et al. |
| 8,192,438 B2 | 6/2012 | Garamszegi |
| 8,216,241 B2 | 7/2012 | Runco et al. |
| 8,608,746 B2 | 12/2013 | Kolb et al. |
| 8,647,347 B2 | 2/2014 | Runco et al. |
| 8,709,044 B2 | 4/2014 | Chao et al. |
| 8,845,700 B2 | 9/2014 | Kwak et al. |
| 8,888,777 B2 | 11/2014 | Mullaney |
| 9,095,379 B2 | 8/2015 | Chao et al. |
| 9,795,416 B2 | 10/2017 | Chao et al. |
| 10,172,648 B2 | 1/2019 | Chao et al. |
| 10,314,624 B2 | 6/2019 | Chao et al. |
| 2001/0020169 A1 | 9/2001 | Metz-Stavenhagen |
| 2001/0029376 A1 | 10/2001 | Saler et al. |
| 2002/0035366 A1 | 3/2002 | Walder et al. |
| 2002/0072752 A1 | 6/2002 | Zucherman et al. |
| 2002/0082599 A1 | 6/2002 | Crandall et al. |
| 2002/0095153 A1 | 7/2002 | Jones et al. |
| 2002/0133155 A1 | 9/2002 | Ferree |
| 2002/0143341 A1 | 10/2002 | Biedermann et al. |
| 2002/0151900 A1 | 10/2002 | Glascott |
| 2002/0173789 A1 | 11/2002 | Howland |
| 2003/0009168 A1 | 1/2003 | Beale et al. |
| 2003/0028195 A1 | 2/2003 | Bette |
| 2003/0045875 A1 | 3/2003 | Bertranou et al. |
| 2003/0073995 A1 | 4/2003 | Reed |
| 2003/0083657 A1 | 5/2003 | Drewry et al. |
| 2003/0083747 A1 | 5/2003 | Winterbottom et al. |
| 2003/0088248 A1 | 5/2003 | Reed |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125750 A1 | 7/2003 | Zwimmann et al. |
| 2003/0149438 A1 | 8/2003 | Nichols et al. |
| 2003/0171749 A1 | 9/2003 | Le Couedic et al. |
| 2003/0171756 A1 | 9/2003 | Fallin et al. |
| 2003/0176861 A1 | 9/2003 | Reed |
| 2003/0191370 A1 | 10/2003 | Phillips |
| 2003/0191470 A1 | 10/2003 | Ritland |
| 2003/0199872 A1 | 10/2003 | Markworth et al. |
| 2003/0203488 A1 | 10/2003 | Mehtali et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2004/0002708 A1 | 1/2004 | Ritland |
| 2004/0049189 A1 | 3/2004 | Le Couedic et al. |
| 2004/0049190 A1 | 3/2004 | Biedermann et al. |
| 2004/0049191 A1 | 3/2004 | Markworth et al. |
| 2004/0073215 A1 | 4/2004 | Carli |
| 2004/0092931 A1 | 5/2004 | Taylor et al. |
| 2004/0102789 A1 | 5/2004 | Baughman |
| 2004/0147936 A1 | 7/2004 | Rosenberg et al. |
| 2004/0147937 A1 | 7/2004 | Dunbar et al. |
| 2004/0158257 A1 | 8/2004 | Bonati et al. |
| 2004/0158258 A1 | 8/2004 | Bonati et al. |
| 2004/0172025 A1 | 9/2004 | Drewry et al. |
| 2004/0172057 A1 | 9/2004 | Guillebon et al. |
| 2004/0176779 A1 | 9/2004 | Casutt et al. |
| 2004/0181224 A1 | 9/2004 | Biedermann et al. |
| 2004/0186473 A1 | 9/2004 | Cournoyer et al. |
| 2004/0204711 A1 | 10/2004 | Jackson |
| 2004/0220567 A1 | 11/2004 | Eisermann et al. |
| 2004/0225289 A1 | 11/2004 | Biedermann et al. |
| 2004/0243139 A1 | 12/2004 | Lewis et al. |
| 2004/0254576 A1 | 12/2004 | Dunbar et al. |
| 2004/0267260 A1 | 12/2004 | Mack et al. |
| 2004/0267264 A1 | 12/2004 | Konieczynski et al. |
| 2004/0267275 A1 | 12/2004 | Cournoyer et al. |
| 2005/0015094 A1 | 1/2005 | Keller |
| 2005/0015095 A1 | 1/2005 | Keller |
| 2005/0021031 A1 | 1/2005 | Foley et al. |
| 2005/0033291 A1 | 2/2005 | Ebara |
| 2005/0033295 A1 | 2/2005 | Wisnewski |
| 2005/0033299 A1 | 2/2005 | Shluzas |
| 2005/0055031 A1 | 3/2005 | Lim |
| 2005/0059969 A1 | 3/2005 | McKinley |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0066514 A1 | 3/2005 | Chau et al. |
| 2005/0070917 A1 | 3/2005 | Justis |
| 2005/0079909 A1 | 4/2005 | Singhaseni |
| 2005/0085813 A1 | 4/2005 | Spitler et al. |
| 2005/0085815 A1 | 4/2005 | Harms et al. |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0137593 A1 | 6/2005 | Gray |
| 2005/0143737 A1 | 6/2005 | Pafford et al. |
| 2005/0143749 A1 | 6/2005 | Zalenski et al. |
| 2005/0149036 A1 | 7/2005 | Varieur et al. |
| 2005/0149048 A1 | 7/2005 | Leport et al. |
| 2005/0149053 A1 | 7/2005 | Varieur et al. |
| 2005/0154389 A1 | 7/2005 | Selover et al. |
| 2005/0159650 A1 | 7/2005 | Raymond et al. |

(56) References Cited

U.S. PATENT DOCUMENTS

| | | |
|---|---|---|
| 2005/0177163 A1 | 8/2005 | Abdou |
| 2005/0192570 A1 | 9/2005 | Jackson |
| 2005/0192573 A1 | 9/2005 | Abdelgany et al. |
| 2005/0192579 A1 | 9/2005 | Jackson |
| 2005/0192589 A1 | 9/2005 | Raymond et al. |
| 2005/0222570 A1 | 10/2005 | Jackson |
| 2005/0228376 A1 | 10/2005 | Boomer et al. |
| 2005/0228380 A1 | 10/2005 | Moore |
| 2005/0228392 A1 | 10/2005 | Keyer et al. |
| 2005/0228400 A1 | 10/2005 | Chao et al. |
| 2005/0234449 A1 | 10/2005 | Aferzon |
| 2005/0245928 A1 | 11/2005 | Colleran et al. |
| 2005/0261687 A1 | 11/2005 | Garamszegi et al. |
| 2005/0261702 A1 | 11/2005 | Oribe et al. |
| 2005/0283244 A1 | 12/2005 | Gordon |
| 2005/0288668 A1 | 12/2005 | Brinkhaus |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036255 A1 | 2/2006 | Pond et al. |
| 2006/0036260 A1 | 2/2006 | Runco et al. |
| 2006/0069391 A1 | 3/2006 | Jackson |
| 2006/0074418 A1 | 4/2006 | Jackson |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Play |
| 2006/0149236 A1 | 7/2006 | Barry |
| 2006/0155277 A1 | 7/2006 | Metz-Stavenhagen |
| 2006/0166534 A1 | 7/2006 | Brumfield et al. |
| 2006/0166535 A1 | 7/2006 | Brumfield et al. |
| 2006/0173454 A1 | 8/2006 | Spitler et al. |
| 2006/0195092 A1 | 8/2006 | Barry |
| 2006/0200131 A1 | 9/2006 | Chao et al. |
| 2006/0200132 A1 | 9/2006 | Chao et al. |
| 2006/0217735 A1 | 9/2006 | MacDonald et al. |
| 2006/0229605 A1 | 10/2006 | Olsen |
| 2006/0229614 A1 | 10/2006 | Foley et al. |
| 2006/0247630 A1 | 11/2006 | Iott et al. |
| 2006/0264934 A1 | 11/2006 | Fallin |
| 2006/0271050 A1 | 11/2006 | Piza Vallespir |
| 2006/0282073 A1 | 12/2006 | Simanovsky |
| 2006/0293690 A1 | 12/2006 | Abdelgany |
| 2006/0293692 A1 | 12/2006 | Whipple et al. |
| 2007/0078460 A1 | 4/2007 | Frigg |
| 2007/0093849 A1 | 4/2007 | Jones et al. |
| 2007/0100347 A1 | 5/2007 | Stad et al. |
| 2007/0118118 A1* | 5/2007 | Kwak et al. ............ 606/61 |
| 2007/0129731 A1 | 6/2007 | Sicvol et al. |
| 2007/0161994 A1* | 7/2007 | Lowery et al. .......... 606/61 |
| 2007/0161998 A1 | 7/2007 | Whipple |
| 2007/0162009 A1 | 7/2007 | Chao et al. |
| 2007/0162010 A1 | 7/2007 | Chao et al. |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0191836 A1 | 8/2007 | Justis |
| 2007/0213715 A1 | 9/2007 | Bridwell et al. |
| 2007/0213716 A1 | 9/2007 | Lenke et al. |
| 2007/0213722 A1 | 9/2007 | Jones et al. |
| 2007/0231059 A1 | 10/2007 | Mullaney |
| 2007/0233079 A1 | 10/2007 | Fallin et al. |
| 2007/0233097 A1 | 10/2007 | Anderson et al. |
| 2007/0260261 A1 | 11/2007 | Runco et al. |
| 2007/0270880 A1 | 11/2007 | Lindemann et al. |
| 2007/0282337 A1 | 12/2007 | Garamszegi |
| 2008/0045956 A1 | 2/2008 | Songer et al. |
| 2008/0077134 A1 | 3/2008 | Dziedzic et al. |
| 2008/0077135 A1 | 3/2008 | Stad et al. |
| 2008/0086130 A1 | 4/2008 | Lake et al. |
| 2008/0161853 A1* | 7/2008 | Arnold et al. .......... 606/246 |
| 2008/0161863 A1* | 7/2008 | Arnold et al. .......... 606/319 |
| 2008/0172062 A1 | 7/2008 | Donahue et al. |
| 2008/0195159 A1 | 8/2008 | Kloss et al. |
| 2008/0243190 A1 | 10/2008 | Dziedzic et al. |
| 2008/0255574 A1 | 10/2008 | Dye |
| 2008/0288005 A1 | 11/2008 | Jackson |
| 2009/0005815 A1* | 1/2009 | Ely ............... A61B 17/7038 606/246 |
| 2009/0018541 A1 | 1/2009 | Lavi |
| 2009/0030419 A1 | 1/2009 | Runco et al. |
| 2009/0030420 A1 | 1/2009 | Runco et al. |
| 2009/0054902 A1 | 2/2009 | Mickiewicz et al. |
| 2009/0062857 A1 | 3/2009 | Ramsay et al. |
| 2009/0082811 A1 | 3/2009 | Stad et al. |
| 2009/0088764 A1 | 4/2009 | Stad et al. |
| 2009/0138056 A1 | 5/2009 | Anderson et al. |
| 2009/0143828 A1 | 6/2009 | Stad et al. |
| 2009/0228051 A1 | 9/2009 | Kolb et al. |
| 2009/0228053 A1 | 9/2009 | Kolb et al. |
| 2009/0281579 A1 | 11/2009 | Weaver et al. |
| 2010/0042155 A1* | 2/2010 | Biedermann ...... A61B 17/7004 606/254 |
| 2010/0063544 A1 | 3/2010 | Butler |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0077689 A1 | 3/2011 | Mickiewicz et al. |
| 2011/0093022 A1 | 4/2011 | Runco et al. |
| 2011/0144695 A1 | 6/2011 | Rosenberg et al. |
| 2011/0196431 A1 | 8/2011 | Chao et al. |
| 2011/0282402 A1 | 11/2011 | Chao et al. |
| 2012/0253413 A1 | 10/2012 | Runco et al. |
| 2014/0188182 A1 | 7/2014 | Chao et al. |
| 2014/0277198 A1 | 9/2014 | Stad |
| 2015/0297268 A1 | 10/2015 | Chao et al. |
| 2017/0156765 A1 | 6/2017 | Chao et al. |
| 2018/0008319 A1 | 1/2018 | Chao et al. |
| 2019/0216509 A1 | 7/2019 | Chao et al. |
| 2019/0307492 A1 | 10/2019 | Chao et al. |

FOREIGN PATENT DOCUMENTS

| | | |
|---|---|---|
| DE | 4107480 A1 | 9/1992 |
| DE | 4238339 A1 | 5/1994 |
| DE | 10005385 A1 | 8/2001 |
| DE | 10005386 A1 | 8/2001 |
| DE | 20207851 U1 | 11/2002 |
| EP | 0381588 B2 | 8/1990 |
| EP | 0441729 B1 | 8/1991 |
| EP | 0487895 A1 | 6/1992 |
| EP | 0558883 A1 | 9/1993 |
| EP | 0572790 B1 | 12/1993 |
| EP | 0592266 A1 | 4/1994 |
| EP | 328883 B1 | 7/1994 |
| EP | 0669109 B1 | 8/1995 |
| EP | 558883 B1 | 7/1997 |
| EP | 0880344 B1 | 12/1998 |
| EP | 0885598 A2 | 12/1998 |
| EP | 0948939 A2 | 10/1999 |
| EP | 0951246 B1 | 10/1999 |
| EP | 1023873 A2 | 8/2000 |
| EP | 1090595 A2 | 4/2001 |
| EP | 784693 B1 | 10/2001 |
| EP | 1295566 A1 | 3/2003 |
| EP | 1364622 B1 | 11/2003 |
| EP | 1574175 A1 | 9/2005 |
| FR | 2677242 | 12/1992 |
| FR | 2680314 A1 | 2/1993 |
| FR | 2729291 A1 | 7/1996 |
| WO | 90/02527 A1 | 3/1990 |
| WO | 9621396 A1 | 7/1996 |
| WO | 98/22033 A1 | 5/1998 |
| WO | 98/25534 A1 | 6/1998 |
| WO | 99/44527 A1 | 9/1999 |
| WO | 01/45576 A1 | 6/2001 |
| WO | 02/07622 A1 | 1/2002 |
| WO | 02/102259 A2 | 12/2002 |
| WO | 03/007828 A1 | 1/2003 |
| WO | 03/032863 A2 | 4/2003 |
| WO | 03/049629 A1 | 6/2003 |
| WO | 03096915 A1 | 11/2003 |

(56) References Cited

FOREIGN PATENT DOCUMENTS

| | | |
|---|---|---|
| WO | 2004004549 A2 | 1/2004 |
| WO | 04/019755 A2 | 3/2004 |
| WO | 04/034916 A1 | 4/2004 |
| WO | 2005006948 A2 | 1/2005 |
| WO | 05/013839 A2 | 2/2005 |
| WO | 05/030065 A1 | 4/2005 |
| WO | 05/044117 A2 | 5/2005 |
| WO | 05/044123 A1 | 5/2005 |
| WO | 2005072081 A2 | 8/2005 |
| WO | 2006020443 A1 | 2/2006 |
| WO | 06/084443 A1 | 8/2006 |
| WO | 2007092797 A2 | 8/2007 |
| WO | 2007092870 A2 | 8/2007 |
| WO | 2007092876 A2 | 8/2007 |
| WO | 2007149426 A2 | 12/2007 |
| WO | 2008024937 A2 | 2/2008 |

OTHER PUBLICATIONS

International Search Report and Written Opinion for Application No. PCT/US06/40621, dated May 18, 2007.
International Search Report for Application No. PCT/US06/40621, dated May 18, 2007.
International Search Report for Application No. PCT/US06/05811, dated Sep. 13, 2007.
European Office Action for Application No. 06736870, dated Dec. 18, 2009.
European Office Action for Application No. 06735464.7, dated Apr. 14, 2010.
European Office Action for Application No. 06735464.7, 4 pages, dated Feb. 10, 2012.
Sofamor Introducteur Contreur De Tige, Schematic Drawings, 7 pages, Jun. 1994.
International Search Report and Written Opinion issued in International Application No. PCT/US06/07619 dated Apr. 16, 2007, 3 pages.
U.S. Appl. No. 16/217,329, filed Dec. 12, 2018, Nam T. Chao.
U.S. Appl. No. 15/711,380, filed Sep. 21, 2017, Nam T. Chao.
U.S. Appl. No. 14/754,259, filed Jun. 29, 2015, Nam T. Chao.
U.S. Appl. No. 13/087,777, filed Apr. 15, 2011, Nam T. Chao.
U.S. Appl. No. 11/073,325, filed Mar. 4, 2005, Nam T. Chao.
U.S. Appl. No. 16/436,471, filed Jun. 10, 2019, Nam T. Chao.
U.S. Appl. No. 15/434,899, filed Feb. 16, 2017, Nam T. Chao.
U.S. Appl. No. 14/200,891, filed Mar. 7, 2014, Nam T. Chao.
U.S. Appl. No. 13/188,161, filed Jul. 21, 2011, Nam T. Chao.
U.S. Appl. No. 11/707,471, filed Feb. 16, 2007, Nam T. Chao.
U.S. Appl. No. 11/073,352, filed Mar. 4, 2005, Nam T. Chao.
U.S. Appl. No. 11/707,696, filed Feb. 16, 2007, Nam T. Chao.

* cited by examiner

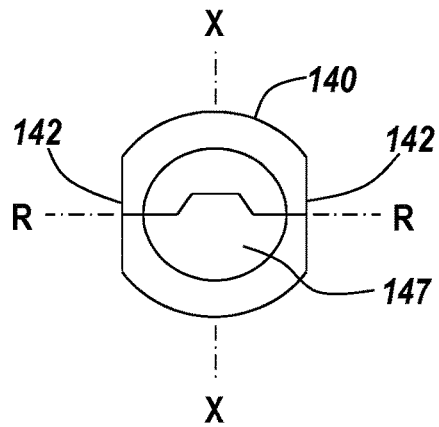
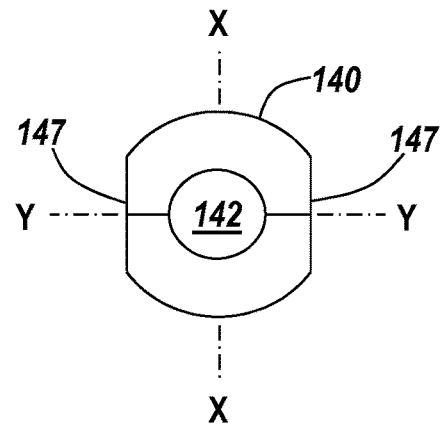
*Fig. 5A*     *Fig. 5B*
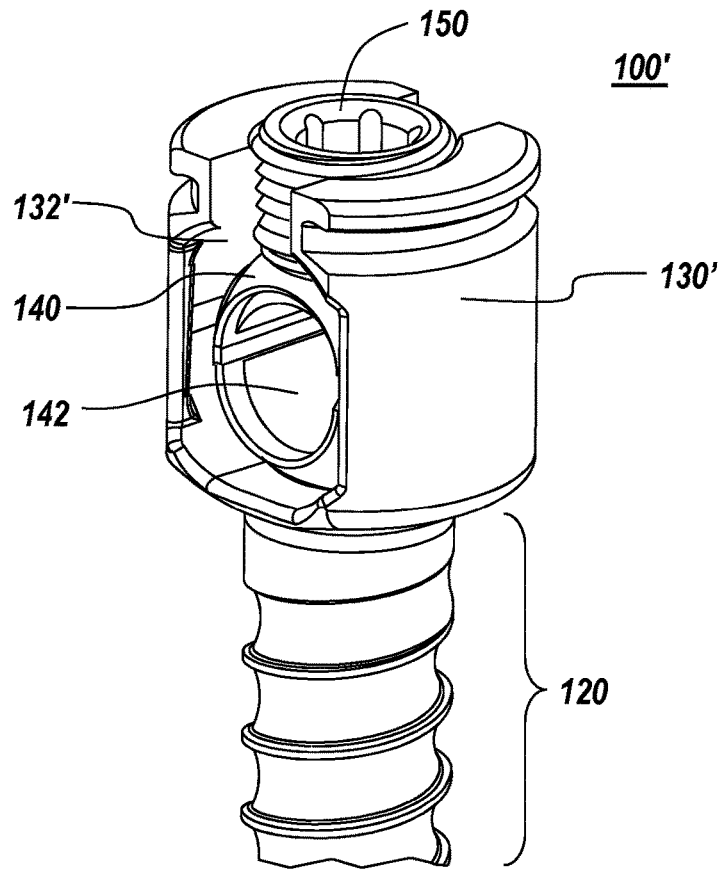
*Fig. 6*

ADJUSTABLE IMPLANT ASSEMBLY

BACKGROUND OF THE INVENTION

Spinal fixation systems may be used in surgery to align, adjust and/or fix portions of the spinal column, (i.e. vertebrae) and/pelvis in a desired spatial relationship relative to each other. Many spinal fixation systems employ a spinal rod for supporting the spine and/or pelvis and for properly positioning components of the spine and/or pelvis for various treatment purposes. Anchors, comprising pins, bolts, screws, and hooks, engage the vertebrae and/or pelvis and connect the supporting spinal fixation element, such as a rod, to the engaged vertebral or pelvic body. The size, length and shape of the cylindrical rod depend on the size, number and position of the vertebral or pelvic body to be held in a desired spatial relationship relative to each other by the apparatus.

Spinal fixation elements can be anchored to specific portions of the vertebra or pelvis. Since the vertebral or pelvic bodies varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a bone, and a head portion having a spinal fixation element-receiving portion. A set-screw, plug, cap or similar type of closure mechanism is used to lock the spinal fixation element into the rod-receiving portion of the pedicle screw. In use, the shank portion of each screw is threaded into a vertebral or pelvic body, and once properly positioned, a spinal fixation rod is seated through the spinal fixation element receiving portion of each screw. The rod is locked into place by tightening a cap or similar type of closure mechanism to securely interconnect each screw and the spinal fixation element. Other anchoring devices also include hooks and other types of bone screws.

Monoaxial screws are a type of screw in which the longitudinal axis of the threaded shank is fixed relative to the head portion, or rod slot. The longitudinal axis of the threaded shank may be aligned with the longitudinal axis of the head portion, and/or the threaded shank extends at a fixed angle relative to the head. In fixed pedicle screws, which are used in the pedicle region of the vertebra, the threaded shank is rigidly connected to or integrally formed with the head such that the orientation of the threaded shank is fixed with respect to the head.

Polyaxial pedicle screws allow angulation of one portion of the screw relative to another portion of the screw and the spinal fixation element coupled to one portion of the screw. For example, polyaxial pedicle screws allow for a shaft portion to pivot relative to a rod-receiving portion in all directions about a 360° arc around the rod-receiving portion. Polyaxial screws may be useful for positioning bone anchors on adjacent vertebrae, when the close proximity of adjacent vertebrae can result in interference between the bone anchors. Polyaxial screws allow for pivoting of the screws in any direction out of alignment with each other to avoid such interference.

Polyaxial and multi-axial screws, which allow the screw shank to pivot in all directions about the head portion, can be difficult to control and often result in movement of the screw shank in planes in which movement is not desirable. For example, during vertebral or pelvic body rotation maneuvers, which require application of force to the screw head, it is not desirable for the screw shank to move relative to the screw head.

SUMMARY OF THE INVENTION

Embodiments provide an adjustable implant assembly that provides for controlled adjustment of a spinal connection element, such as a spinal rod, received in a body of the implant assembly relative to the body of the bone screw. The adjustable implant assembly may allow the spinal fixation element received in a receiving portion of the assembly to pivot relative to the body of the bone screw.

According to a first aspect, an implant assembly is provided. The implant assembly includes a bone anchor, a proximal head portion, and a cradle. The bone anchor has a distal shaft extending along a longitudinal axis configured to engage bone. The proximal head portion is connected to the bone anchor. The cradle is mounted within the proximal head portion and configured to receive a spinal fixation element. The cradle can move relative to the proximal head portion allowing the spinal fixation element to pivot relative to the head portion According to another aspect, a method is provided. First a first implant assembly as described herein is inserted into a first vertebral or pelvic body. A first portion of a spinal fixation element is inserted in the cradle of the first implant assembly. Then, the orientation of the spinal fixation element relative to proximal head portion of the first implant assembly is adjusted.

According to another aspect, an implant assembly is provided. The implant assembly includes a bone anchor, a proximal head portion, and a substantially spherical body within the proximal head portion. The bone anchor includes a distal shaft extending along a longitudinal axis configured to engage bone. The proximal head portion connected to the bone anchor and is configured to contain the substantially spherical body. The substantially spherical body is configured to be movable in relation to the proximal head. The substantially spherical body includes a lower element defining a lower portion of a central bore and an upper element defining an upper portion of the central bore and configured to mate with the lower portion to form a central bore for receiving a spinal fixation element.

BRIEF DESCRIPTION OF THE DRAWINGS

FIGS. 5A and 5B illustrate an alternate cradle configuration according to another embodiment of the invention;

FIG. 6 illustrates an alternate proximal head configuration according to another embodiment of the invention.

DETAILED DESCRIPTION OF THE INVENTION

Figure 1:
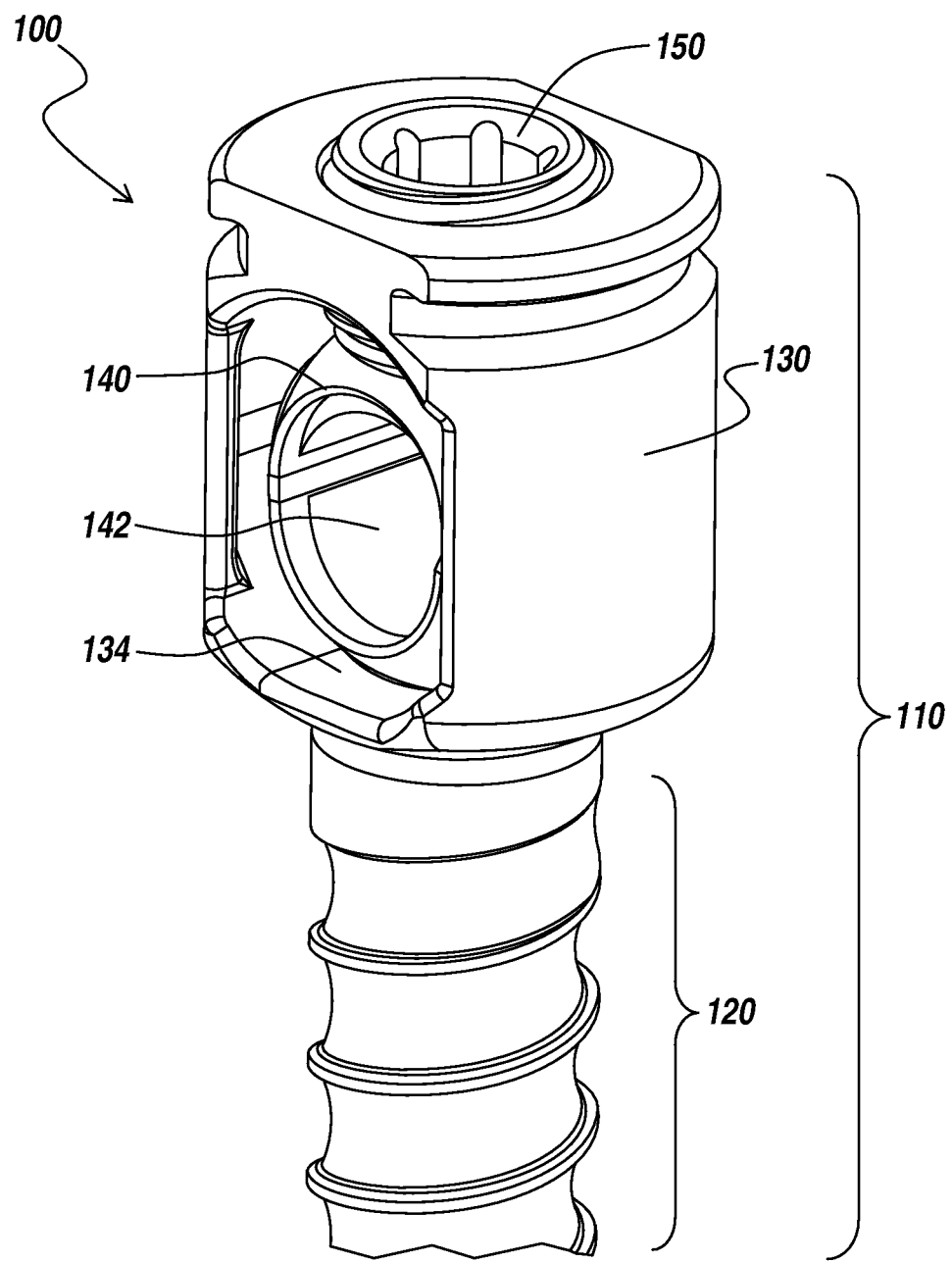
FIG. 1 illustrates an implant assembly according to an illustrative embodiment of the invention.

An implant assembly includes a screw body, including anchor portion and proximal head portion, and a cradle movably mounted in the screw body to allow for controlled angulation between a spinal connection element disposed in the cradle and the screw body. The cradle is pivotable in one or more selected directions about one or more axes relative to the screw body. The cradle may be generally, substantially spherical in shape and allow for unrestricted movement in one or more directions around one or more axis.

During spinal deformity surgeries, it may be necessary to de-rotate the vertebral or pelvic bodies to normalize the spine. Due to varying patient anatomy, insertion of fixed angle screws, where the anchor portion of the screw extends at a fixed angle relative to the rod-receiving portion of the screw can be difficult. Polyaxial and multi-axial screws, which allow the screw shank to pivot in all directions about the head portion, can be difficult to control and often result in undesirable movement in certain planes. An adjustable implant assembly allows for angulation of a spinal fixation element relative to the body of the screw that receives the spinal rod or other implant therein. For example, the implant assembly described herein allows for angulation of a spinal fixation element relative to the body of the screw. In certain embodiments, an adjustable implant assembly may be uniaxial and permit movement about a single selected axis.

The adjustable implant assembly disclosed may allow a surgeon to rotate vertebral or pelvic bodies and facilitates placement of the spinal fixation element. The adjustable implant assembly allows for a surgeon to achieve an ideal orientation of the spinal fixation element relative to the bone screw, without requiring the spinal fixation element to have a predetermined, fixed orientation, or necessarily be perpendicular to the longitudinal axis of the screw shank.

The exemplary adjustable implant assemblies of the illustrative embodiments may be employed to engage one or more spinal fixation elements to bone. For example, an implant assembly may be employed to fix a spinal plate, rod, and/or cable to a vertebra of the spine. Although the exemplary implant assemblies described below are designed primarily for use in spinal applications, one skilled in the art will appreciate that the structure, features and principles of the exemplary implant assemblies, as well as the other exemplary embodiments described below, may be employed to couple any type of orthopedic implant to any type of bone or tissue.

The illustrative adjustable implant assembly may be used to attach a non-rigid member to bone. For example, the adjustable implant assembly may be used to attach a rod, ligament, bar, cable or other non-rigid member extending between and connecting two bone screws, for example for connecting superior and inferior vertebra. Alternatively, the implant assembly may be used to attach a rigid member to bone. While the invention will be described with respect to an implant assembly that receives a spinal rod that is movably relative to the implant assembly, the invention is not limited to spinal rods and may be used with any suitable spinal connection element to be coupled to bone.

According to one aspect of the invention, an implant assembly 100, an embodiment of which is shown in FIGS. 1, is provided to allow movement of a spinal rod relative to a bone screw body. The implant assembly 100 has a screw body 110, which includes a distal anchor portion 120 for anchoring the screw assembly to bone and a proximal head portion 130. A cradle 140 for receiving a spinal fixation element (not shown) is seated in the proximal head 130 and is configured to move relative to the proximal head 130. In certain embodiments, the implant assembly 100 further includes a locking mechanism 150 for securing the position of the cradle 140 and a spinal fixation element relative to the proximal head 130. Each of these elements will be described in more detail below.

Figure 2:
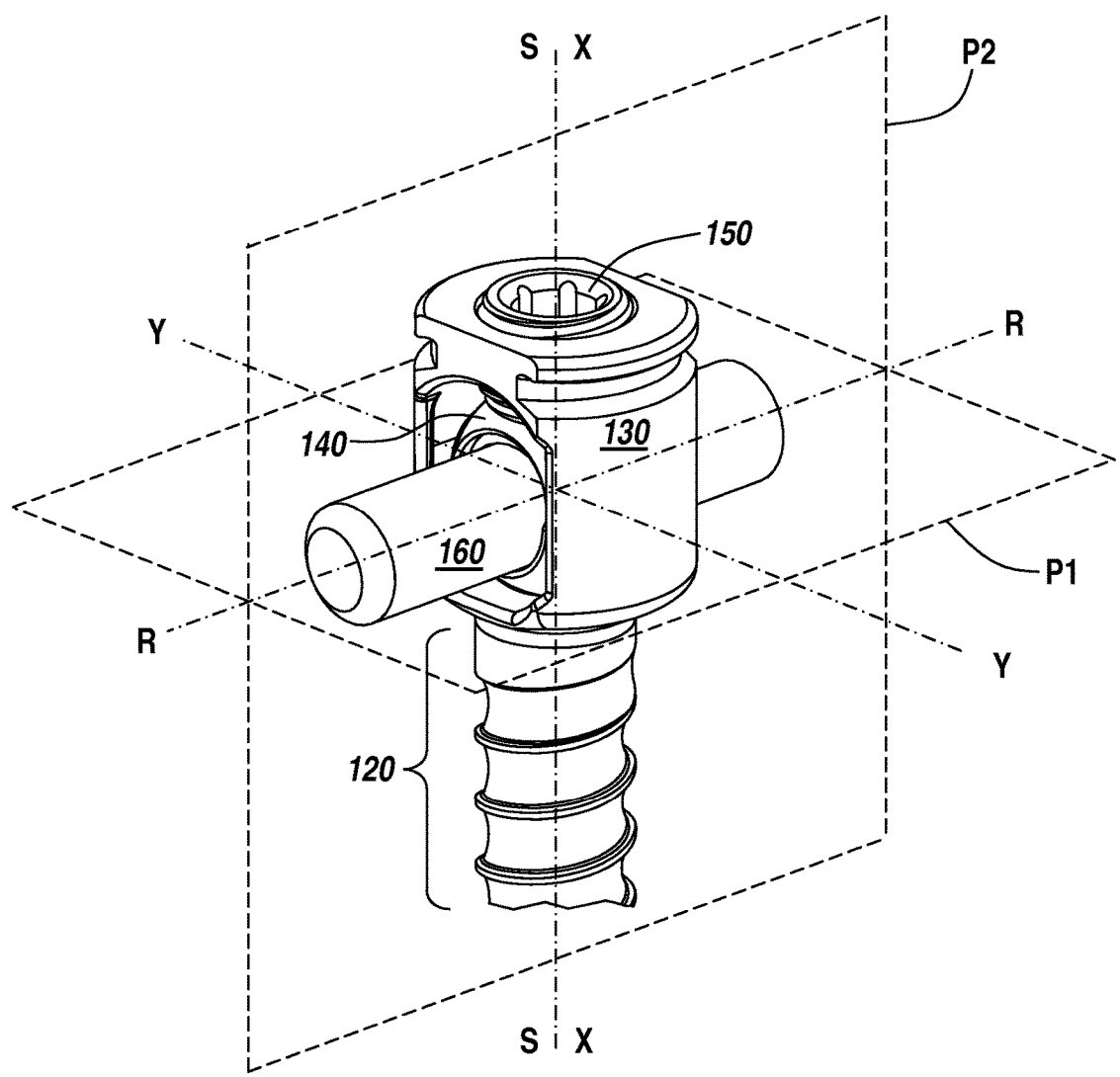
FIG. 2 illustrates an assembled implant assembly including a spinal rod movably received therein according to an illustrative embodiment of the invention.

FIG. 2 shows the bone anchor assembly 100 used in conjunction with a spinal fixation element 160, in this case a spinal rod. The orientation of the cradle 140 may be selectively adjusted to controllably adjust the orientation of the spinal rod 160 relative to the screw body 110 of the implant assembly 100. Preferably, the cradle 140 allows for pivoting of the spinal rod 160 about one or more axes in one or more directions relative to the screw body 110 of the screw assembly 100. For example, the cradle 140 may allow the spinal rod 160 to pivot about a first axis X-X and/or a second axis Y-Y relative to the proximal head portion 130.

The cradle may have a central bore 142 that extends along an axis R-R, which defines and corresponds to the longitudinal axis of the spinal rod 160. In a default position, the axis R-R is preferably perpendicular to the longitudinal axis S-S of the body 110, though one skilled in the art will recognize that the cradle may have any suitable default orientation.

In the illustrative embodiment, the axis X-X extends through the center of the cradle 140, perpendicular to the axis R-R and aligns with the longitudinal axis S-S when the cradle is in a default position, so that the spinal rod 160 sweeps through a first plane P1. The illustrative first plane P1 is substantially parallel to the coronal plane of the body when the implant assembly 100 is employed in a patient. However, one skilled in the art will recognize that the first axis X-X about which the spinal rod 160 can pivot may have any suitable orientation and is not limited to the illustrative orientation.

The spinal rod 160 may also or alternatively pivot in a second plane P2 about axis Y-Y. In the illustrative embodiment, the axis Y-Y extends substantially perpendicular to the axis X-X, the axis S-S, and the axis R-R of the spinal rod 160 when the cradle 140 is in a default position, though one skilled in the art will recognize that the second axis about which the spinal rod 160 can pivot may have any suitable orientation. The plane P2 corresponds to the sagittal plane in a body when the illustrative biaxial implant assembly is implanted in the body. However, one skilled in the art will recognize that the second axis Y-Y about which the spinal rod 160 can pivot may have any suitable orientation and is not limited to the illustrative orientation.

The spinal rod 160 may be rotated by a selected amount about only the X-X axis, only the Y-Y axis, or both axis. The rotation about one axis may cause the orientation of the other axis to shift, or the orientation of each axis X-X and Y-Y may be fixed independently of the orientation of the other axis.

Figure 3A:
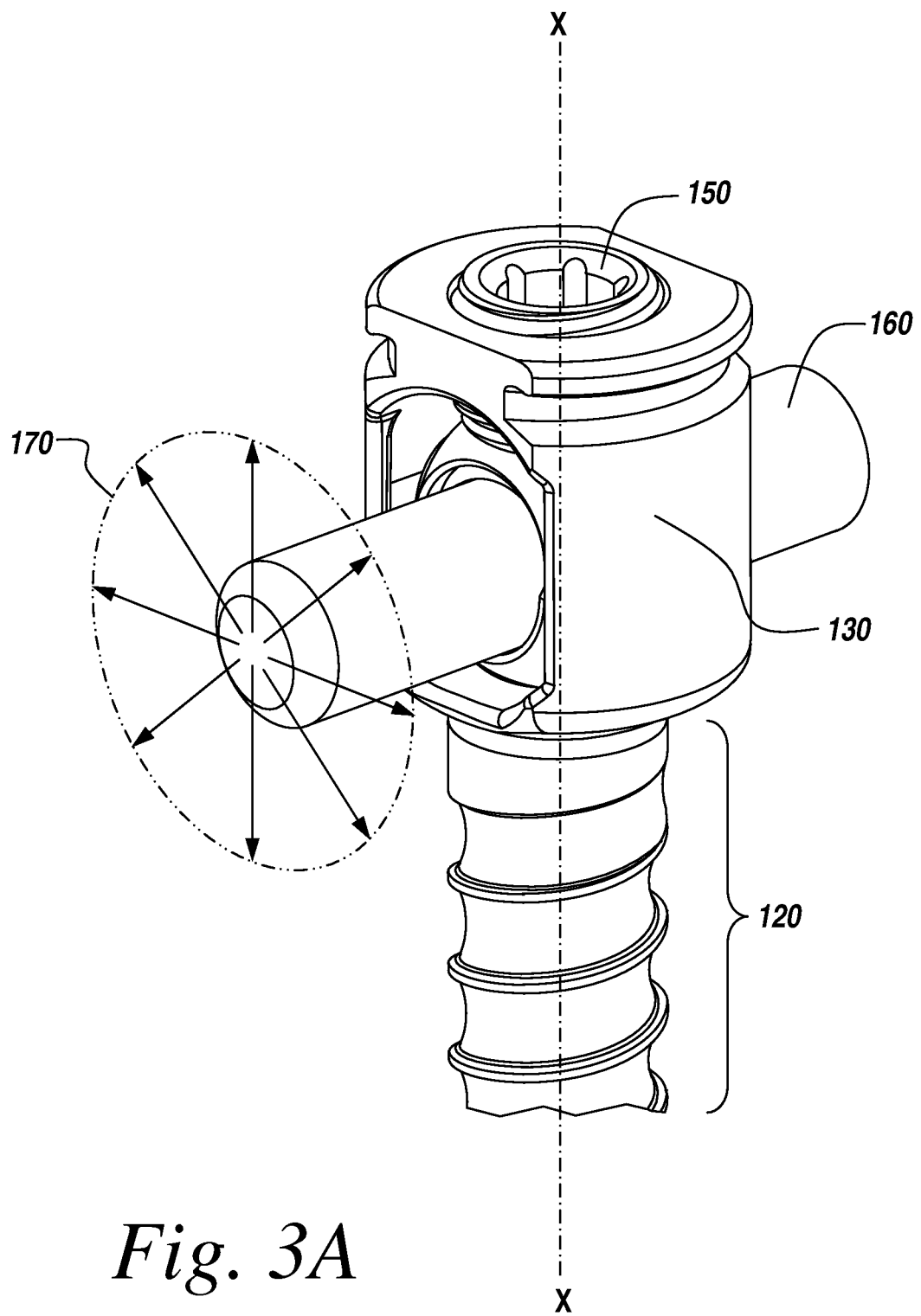
FIGS. 3A and 3B illustrate possible ranges of motion of the spinal rod relative to the bone screw body according to different embodiments of the invention.
Figure 3B:
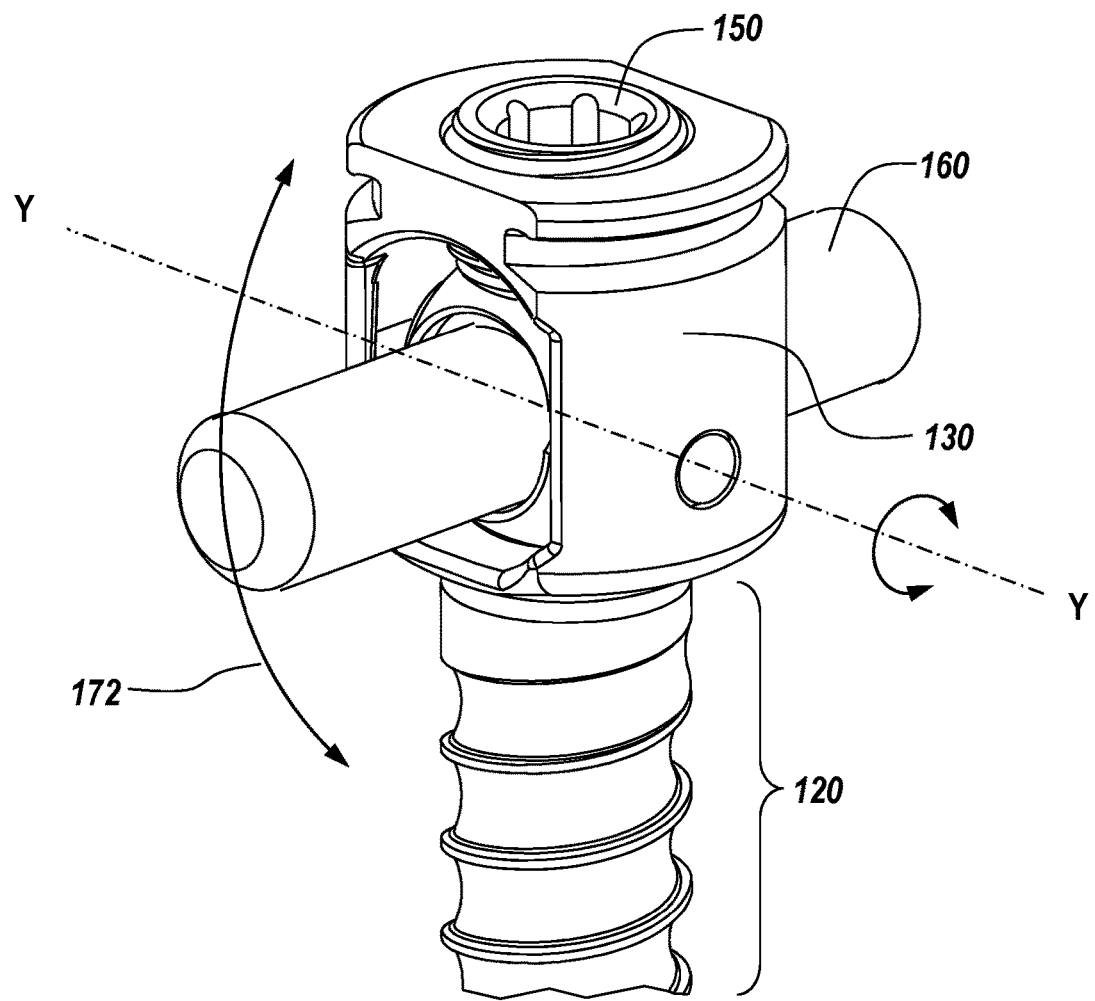

FIGS. 3A and 3B illustrate possible varieties of movement of the spinal rod 160 relative to the bone screw body according to different embodiments of the invention. The implant assembly may be poly-axial as shown in FIG. 3A. The spinal rod 160 of FIG. 3A may pivot through a cone of motion 170 defining the possible orientations of the spinal rod 160 relative to the body 110 through rotation about the X-X and/or Y-Y axis. Alternatively, the implant assembly may be monoaxial as shown in FIG. 3B. The spinal rod 160 of FIG. 3B may be confined to path 172 about the Y-Y axis.

In addition, for cylindrical rods or other spinal connection elements, the rod 160 may be rotated about axis R-R and/or slide within the cradle 140, providing an additional degree of freedom for attaining a selected orientation of the spinal rod relative to the screw body 110.

Figure 4:
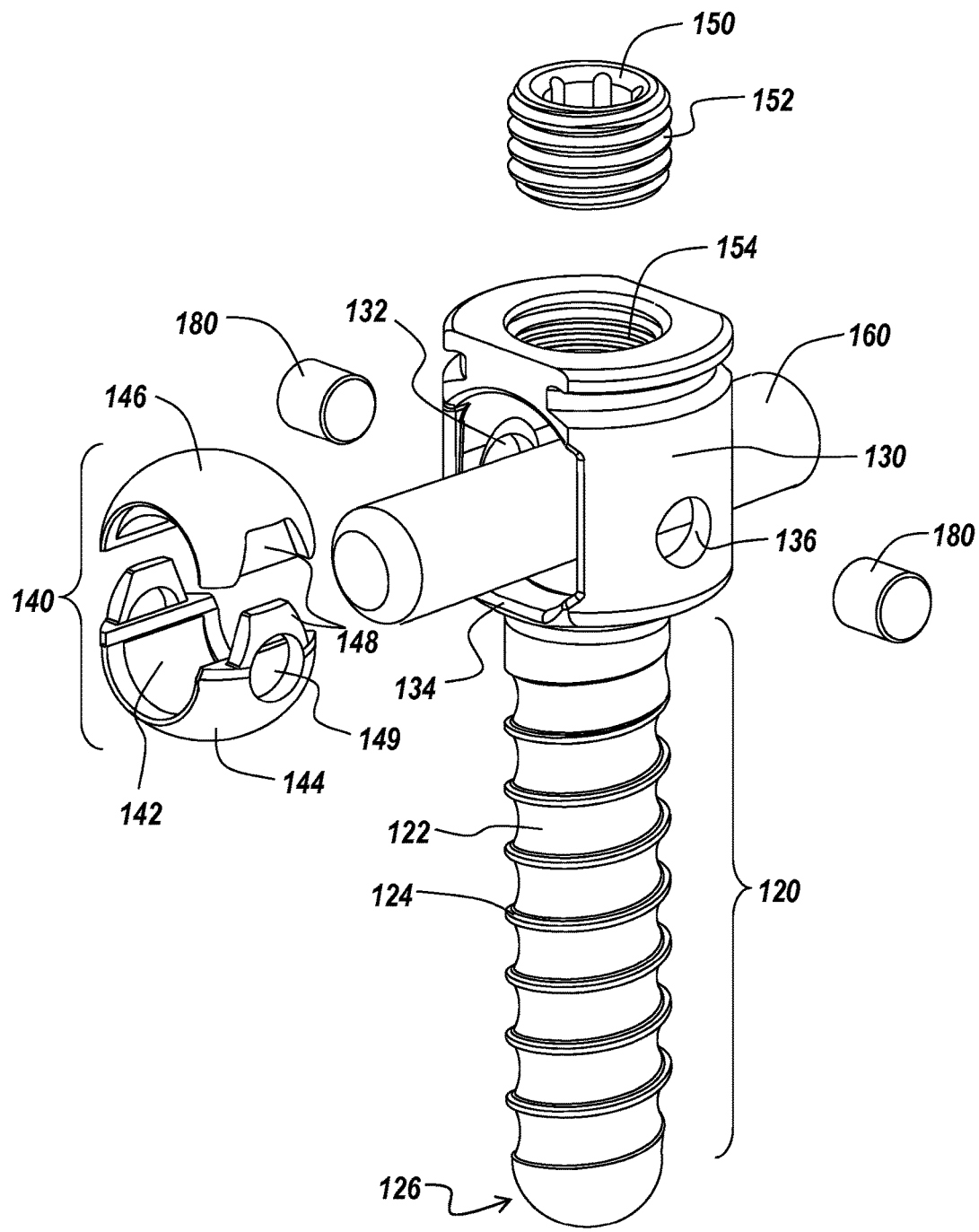
FIG. 4 is an exploded view of an implant assembly according to one embodiment of the invention.

FIG. 4 is an exploded view of the exemplary implant assembly 100, illustrating the individual components of the assembly 100 that facilitate the adjustability according to an illustrative embodiment of the invention.

The anchor portion 120 of the screw assembly can have any suitable size, configuration and shape. The bone anchor 120 comprises a distal shaft 122 configured to engage bone. The distal shaft 122 of the bone anchor 120 extends along the longitudinal axis S-S. The distal shaft 122 may include one or more bone engagement mechanisms to facilitate gripping engagement of the bone anchor to bone. In the illustrated embodiment, the distal shaft 122 includes an external thread 124 extending along at least a portion of the shaft for engaging bone. In the illustrated embodiment, the external thread 124 is a single lead thread that extends from a distal tip 126 of the shaft to the proximal head portion 130, though one skilled in the art will recognize that the external thread may extend along any selected portion of the shaft and have any suitable number of leads. Other suitable bone engagement mechanisms include, but are not limited to, one or more annular ridges, multiple threads, dual lead threads, variable pitched threads, hole, slots, fenestrations, and/or any conventional bone engagement mechanism.

The proximal head portion 130 is sized and configured to receive a spinal fixation element 160 as well as the cradle 140. In this embodiment, the proximal head portion 130 is a closed-type screw head. The illustrative head portion 130 defines a central bore 132 for receiving the cradle 140 and the spinal rod 160. The central bore may be further shaped and dimensioned to allow the cradle 140 to move freely relative to the proximal head 130 when the cradle 140 is within the central bore 132. For example, the illustrative cradle is generally substantially spherical in shape. As such, the central bore may have a concave portion for receiving a generally substantially spherical shape. In certain embodiments, the ends 134 of the central bore 132 may be chamfered or rounded to allow for greater freedom of movement of a spinal fixation device 160 inserted in the proximal head portion 130.

As shown, the proximal head portion 130 may be rigidly coupled to or integral with the anchor portion 120 to form the screw body 110, though one skilled in the art will recognize that the proximal head portion 130 may alternatively be movably coupled to the anchor portion 120 to provide additional adjustability.

The longitudinal axis S-S of the bone anchor portion 120 preferably aligns with a longitudinal axis extending through the proximal head portion 130. However, one skilled in the art will recognize that the proximal head portion 130 may alternatively be offset from or extend at a selected angle relative to the anchor portion 120.

The cradle 140 allows for pivoting of the spinal fixation element 160 about a first axis X-X and/or a second axis Y-Y. In this example, the cradle 140 comprises a generally substantially spherical body with a central bore 142 for receiving the spinal fixation element 160. In certain embodiments, the cradle may include a lower element 144 and an upper element 146 that are combined to form the generally substantially spherical body of the cradle 140.

In this embodiment, the lower element 144 is half sphere shape and forms half of the generally substantially spherical boy of the cradle 140. The lower element 144 further defines a lower portion of the central bore 142. In this embodiment, the upper element 146 is half sphere in shape and forms the other corresponding half of the generally substantially spherical boy of the cradle 140. The upper element 146 also defines the upper portion of the central bore 142. When the upper element 146 is mated with the lower element 144, they form the generally substantially spherical body with a central bore 142. The spinal fixation element 160 is received in the central bore 142 between the lower and upper elements 144, 146. The central bore 142 is sized and dimensioned to capture the spinal fixation element 160 when the lower and upper elements 144, 146 are fully mated. In certain embodiments, the upper and lower elements 144, 146 of the cradle 140 may further include interlocking surface configuration 148 to assist in the mating of the lower and upper elements 144, 146. One skilled in the art will understand that other shapes, geometries, and configurations are possible.

While the generally substantially spherical shape of the cradle 140 allows for poly-axial movement, in certain embodiments, mono-axial movement may be desired. As such, cradle 140 may be provided with pivot points to restrict the movement of the cradle 140 to a first axis. An example of this can be seen in FIG. 4. Here the pivot pins 180 are provided to mate the cradle 140 and proximal head portion 130 and provide a pivot point along a first axis, such as the Y-Y axis. In this embodiment, the proximal head 130 is provided with thru-holes 136 and the cradle 140 has recesses 149 for receiving the pivot pins 180. When inserted, the pivot pins 180 pass through the thru-holes 136 of the proximal head portion 130 and engage the recesses 149 of the cradle 140. The pivot pins 180 provide a pivot point that allows movement in one around one axis, such as axis Y-Y.

While, the pivot points in this embodiment were provided by separate pivot pins 180 is should be understood that other pivot configuration are possible. For example, the pivot points may be formed by interlocking surface configurations one the cradle 140 and central bore 132 of the proximal head portion 130. In other embodiments, the generally substantially spherical body may include flat portions on opposite sides of the body to restrict movement of the cradle in the proximal head portion to a first axis.

In use, the spinal fixation element 160, such as a rod, is received in the central bore 142 of the cradle 140. The cradle 140, in turn resides in the central bore 132 of the proximal head portion 130. The proximal head portion is attached to the bone anchor 120 of the screw body 110 which is embedded in a bone. Thus, the bone anchor assembly 100 may be used to connect a spinal fixation element 160 to a vertebral or pelvic body. The cradle 140 allows the received spinal fixation element 160 to pivot about one or more selected axes in a selected direction relative to the bone anchor by a selected degree, preferably between 0° and 90°. Once the spinal fixation element 160 is in a desired orientation, a user may lock the orientation of the spinal fixation element 160 relative to the screw body 110 by inserting a locking mechanism, such as the set screw 150.

The locking mechanism secures the cradle 140 and, in turn, the spinal fixation element 160 within the central bore 132 of the proximal head portion and locks the cradle 140 and spinal fixation element 160 in the selected orientation within and relative to the screw body. In the illustrative embodiment, advancement of the locking mechanism into engagement with the upper portion 146 of the cradle 140. The upper element 146 of the cradle 140 engages the spinal fixation element 160 in the central bore 142. The spinal fixation engages the lower element 144 of the cradle 140. The lower element 144 engages a sidewall of the central bore 132 of the proximal head portion 132. Thus, the forces exerted by the side wall of the central bore and the locking mechanism 150 serve to mate the lower and upper elements 144, 146 of the cradle 140 capturing the spinal fixation element 160. The same forces also serve to secure the position of the cradle in the central bore 132.

The locking mechanism 150 may have any suitable size, shape, configuration for securing the spinal fixation element 160 and cradle 140 in a selected orientation relative to the screw body 110. The locking mechanism 150 may be secured to the screw body 110 through any suitable means, such as threads 152 on the locking mechanism 150. The threads 152 engage corresponding threads 154 on the proximal head portion 130. One skilled in the art will recognize that any suitable means for locking the spinal rod in a selected position and orientation relative to the screw body 110 may be used.

FIGS. 5A and 5B depict an example of a cradle configuration in which flat portions 147 are provided on opposite sided of the generally substantially spherical body of the cradle 140. FIG. 5A depicts a side view representation of the cradle 140 wherein one of the flat portions 147 is view head on. FIG. 5B depicts the cradle 140 rotated 90° and the flat portions 147 are on either side central bore 142. When the cradle is in the proximal head portion 130 the flat surfaces 147 restrict the movement of the cradle to around one axis, such as axis Y-Y. The flat surfaces 147 serve to bind the cradle 140 against the central bore 132 of the proximal head restricting movement along around a second axis, such as X-X. Other geometries, shapes, and configurations will be apparent to one skilled in the art.

FIG. 6 depicts another embodiment of an implant assembly 100' having a different proximal head portion configuration. In this example, the proximal head 130' is an open type screw head. As with the previous embodiment, the implant assembly includes a bone anchor 120, proximal head 130' cradle 140 and locking mechanism 150. However, instead of a central bore, the proximal head portion 130' includes a U-shaped slot 132' and a cavity for receiving the cradle 140. The bone anchor 120, cradle 140, and locking mechanism 150 operate as described above.

Figure 7:
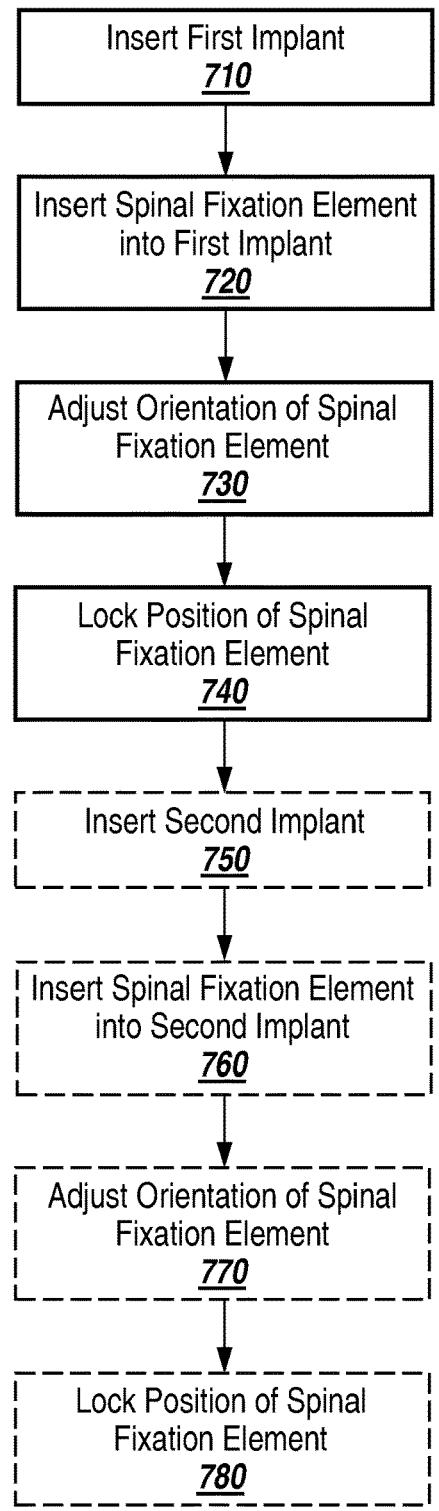
FIG. 7 illustrates an embodiment of a method for connecting a spinal fixation element to one or more vertebral or pelvic bodies using the implant assembly.

FIG. 7 depicts one illustrative embodiment of method 700 of using the implant assembly 100 to attach a spinal fixation element 160 to one or more vertebral or pelvic bodies. A first implant assembly 100 is inserted into a vertebra or pelvic bone of the patient (step 710). A first portion of a spinal fixation element 160, such as a rod, is inserted into the cradle 140 of the first implant assembly 100 (step 720). The orientation of spinal fixation element 160 in relation to the screw body 110 may then be adjusted as desired (step 730). Once the spinal fixation element 160 is in the desired orientation, the position of the cradle 140 and spinal fixation element 160 may be locked using a locking mechanism 150 (step 740).

In certain embodiments, the spinal fixation element 160 may be further connected to other implant assemblies 100 thereby linking the first vertebral or pelvic body to a second vertebral or pelvic body. Thus, a second implant assembly 100 is inserted into the second vertebral or pelvic body (step 750). A second portion of the spinal fixation element 160 may be inserted in cradle 140 of the second implant assembly 100 (step 760). The orientation of spinal fixation element 160 in relation to the second screw body 110 may then be adjusted as desired (step 770). Once the spinal fixation element 160 is in the desired orientation, the position of the cradle 140 and spinal fixation element 160 may be locked using a locking mechanism 150 (step 780). This process may then be performed again with additional implant assemblies.

The components of the biaxial implant assembly of the illustrative embodiments of the invention may be manufactured from any suitable biocompatible material, including, but not limited to, metals and metal alloys such as titanium and stainless steel, polymers and/or ceramics. The components may be manufactured from the same or different materials though manufacturing processes known in the art.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

The invention claimed is:

1. An implant assembly comprising:
a bone anchor having a distal shaft extending along a longitudinal axis configured to engage bone;
a proximal head portion connected to the bone anchor wherein the proximal head portion is a closed-type screw head, wherein the longitudinal axis of the bone anchor aligns with a longitudinal axis extending through the proximal head portion, and the proximal head portion is integral with the bone anchor and includes a central bore;
a cradle within the proximal head portion for receiving a spinal fixation element, wherein the cradle can move relative to the proximal head portion allowing the spinal fixation element to pivot relative to the head portion, wherein the cradle comprises a spherical body with a central bore for receiving the spinal fixation element, the body being formed by an upper element that is a half sphere in shape and a lower element that is a half sphere in shape, wherein the upper element and the lower element have interlocking surface configurations to assist in mating the upper element and lower element; and
a locking mechanism for locking a position of the cradle in the central bore of the proximal head portion and for, in conjunction with side walls of the central bore, mating the upper element and the lower element of the cradle.

2. An implant assembly comprising:
a bone anchor having a distal shaft extending along a longitudinal axis configured to engage bone;
a proximal head portion connected to the bone anchor wherein the proximal head is a closed-type screw head, wherein the longitudinal axis of the bone anchor aligns with a longitudinal axis extending through the proximal head portion, and the proximal head portion is integral with the bone anchor and includes a central bore; and
a spherical body within the proximal head portion configured to be movable in relation to the proximal head, the spherical body comprising:
a lower element defining a lower portion of a central bore, the lower element being a half sphere in shape;
an upper element defining an upper portion of the central bore and configured to be operably coupled with the lower portion to form a central bore for receiving a spinal fixation element, the upper element being a half sphere in shape, wherein the lower element and the upper element include interlocking surface configurations to assist in operably coupling the lower element and the upper element; and
a locking mechanism for locking a position of the cradle in the central bore of the proximal head portion and for, in conjunction with side walls of the central bore, mating the upper element and the lower element of the cradle, wherein the locking mechanism is a set screw that directly contacts the cradle to lock the position of the cradle.

3. The implant assembly of claim 2, wherein the ends of the bore of the proximal head portion are chamfered or rounded to provide clearance for the movement of the spinal fixation element.

* * * * *